United States Patent
Boiteau et al.

(10) Patent No.: US 7,989,483 B2
(45) Date of Patent: Aug. 2, 2011

(54) 4-HETEROARYLIMIDAZOLE-2-THIONE TYROSINASE INHIBITORS AND PHARMACEUTICAL/COSMETIC APPLICATIONS THEREOF

(75) Inventors: Jean Guy Boiteau, Valbonne (FR); Corinne Millois Barbuis, Saint Raphael (FR); Karine Bouquet, St. Laurent du Var (FR)

(73) Assignee: Galderma Research & Development, Biot (FR)

( * ) Notice: Subject to any disclaimer, the term of this patent is extended or adjusted under 35 U.S.C. 154(b) by 0 days.

(21) Appl. No.: 12/631,309

(22) Filed: Dec. 4, 2009

(65) Prior Publication Data

US 2010/0144813 A1 Jun. 10, 2010

Related U.S. Application Data

(63) Continuation of application No. PCT/FR2008/050995, filed on Jun. 4, 2008.

(30) Foreign Application Priority Data

Jun. 5, 2007 (FR) ...................................... 07 55473

(51) Int. Cl.
*A61K 31/4178* (2006.01)
*C07D 233/20* (2006.01)
(52) U.S. Cl. ................... 514/386; 548/311.1; 548/316.4
(58) Field of Classification Search .................. 514/386; 548/311.1, 316.4
See application file for complete search history.

(56) References Cited

U.S. PATENT DOCUMENTS 4,159,338 A * 6/1979 Cherkofsky et al. .......... 514/397

FOREIGN PATENT DOCUMENTS

| JP | 05124923 | 5/1993 |
| JP | 05132422 | 5/1993 |

* cited by examiner

*Primary Examiner* — Joseph McKane
*Assistant Examiner* — Janet L Coppins
(74) *Attorney, Agent, or Firm* — Buchanan Ingersoll & Rooney, P.C.

(57) ABSTRACT

Novel 4-heteroarylimidazole-2-thione tyrosinase inhibiting compounds corresponding to the following general formula (I):

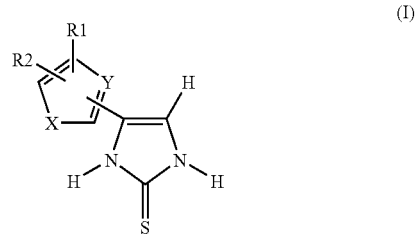

formulated into pharmaceutical or cosmetic compositions are useful for the treatment or prevention of pigmentary disorders, or for preventing and/or treating signs of skin aging, and/or for body or hair hygiene.

14 Claims, 1 Drawing Sheet

4-HETEROARYLIMIDAZOLE-2-THIONE TYROSINASE INHIBITORS AND PHARMACEUTICAL/COSMETIC APPLICATIONS THEREOF

CROSS REFERENCE TO PRIORITY/PCT APPLICATIONS

This application claims priority under 35 U.S.C. §119 of FR 0755473, filed Jun. 5, 2007, and is a continuation/national phase of PCT/FR 2008/050995, filed Jun. 4, 2008 and designating the United States (published in the French language on Dec. 18, 2008 as WO 2008/152332 A1; the title and abstract were also published in English), each hereby expressly incorporated by reference in its entirety and each assigned to the assignee here.

BACKGROUND OF THE INVENTION

1. Technical Field of the Invention

The present invention relates to novel 4-heteroarylimidazole-2-thione compounds as industrial and useful products. It also relates to their process of preparation and to their formulation, as tyrosinase inhibitors, into pharmaceutical or cosmetic compositions useful for the treatment or prevention of pigmentary disorders.

2. Description of Background and/or Related and/or Prior Art

The pigmentation of the skin, in particular human skin, results from the synthesis of melanin by the dendritic cells, the melanocytes. The melanocytes comprise organelles, known as melanosomes, which transfer the melanin into the upper layers of keratinocytes, which are then transported to the surface of the skin via the differentiation of the epidermis.

Among the enzymes of melanogenesis, tyrosinase is a key enzyme which catalyzes the first two stages of the synthesis of melanin. Homozygous tyrosinase mutations result in oculocutaneous albinism type I characterized by a complete absence of the synthesis of melanin.

It is proving to be important to develop novel therapeutic approaches to treat disorders of pigmentation resulting from an increase in the production of melanin, for which there exists no treatment meeting all the expectations of patients and dermatologists.

The majority of skin-lightening compounds already known are phenols/catechols. These compounds inhibit tyrosinase but the majority of them are cytotoxic for the melanocytes as a result of oxidation phenomenon resulting in the formation of quinones responsible for this toxicity. This toxic effect risks bringing about permanent depigmentation of the skin.

SUMMARY OF THE INVENTION

It has now unexpectedly and surprisingly been discovered that novel compounds with the 4-heteroarylimidazole-2-thione structure exhibit a very good inhibitory activity for the enzyme tyrosinase and a very low cytotoxicity.

These compounds find applications in human medicine, in particular in dermatology, and in the field of cosmetics.

Among the heteroarylimidazole-2-thione derivatives already known, some have been described as having anti-inflammatory properties (S. Maeda, M. Suzuki, T. Iwasaki, K. Matsumoto and Y. Iwazawa, *Chem. Pharm. Bull.*, 1984, 32, 7, 2536-2543).

JP05132422 discloses the administration of certain imidazole-2-thiones as tyrosinase inhibitors. However, no imidazole-2-thione derivative substituted in the 4 position by a heteroaryl moiety is described. No inhibitory activity for tyrosinase is shown for compounds with the 4-heteroarylimidazole-2-thione structure. In point of fact, it has unexpectedly and surprisingly been found that certain compounds with the 4-heteroarylimidazole-2-thione structure of the present invention exhibit an inhibitory activity for tyrosinase which is much better than that of the compounds of JP05132422.

Thus, the present invention features novel compounds of the following general formula (I):

(I)

in which:

X is an oxygen atom or a sulfur atom,

Y is a carbon atom or a nitrogen atom, when R2=H, then R1 is:

a $C_1$-$C_7$ alkyl radical, a $C_3$-$C_7$ cycloalkyl radical, with the proviso that one of the carbon atoms of the ring may optionally be replaced by an oxygen or sulfur atom, a $C_4$-$C_9$ cycloalkylalkyl radical, a carboxyl substituent, a ($C_1$-$C_6$ alkoxy)carbonyl radical, or a $C_1$-$C_4$ alkyl radical substituted by a ($C_1$-$C_4$ alkoxy)carbonyl, and, when R2 is other than a hydrogen atom, then $R_1$ and $R_2$, which may be identical or different, are selected from among:

a $C_1$-$C_7$ alkyl radical, a $C_3$-$C_7$ cycloalkyl radical, with the proviso that one of the carbon atoms of the ring may optionally be replaced by an oxygen or sulfur atom, a $C_4$-$C_9$ cycloalkylalkyl radical, a carboxyl substituent, a ($C_1$-$C_6$ alkoxy)carbonyl radical, or a $C_1$-$C_4$ alkyl radical substituted by a ($C_1$-$C_4$ alkoxy)carbonyl radical, and, when R2 is in the ortho position with respect to R1, then R1 and R2 together form a hydrocarbon ring containing 5 or 6 carbon atoms, and the salts and tautomeric forms thereof.

The present invention also relates to the formulation of the compounds of formula (I), or their salts or their tautomeric forms thereof, into pharmaceutical compositions useful for the treatment or prevention of hyperpigmentary disorders.

DETAILED DESCRIPTION OF BEST MODE AND SPECIFIC/PREFERRED EMBODIMENTS OF THE INVENTION

The tautomeric forms can be represented as follows:

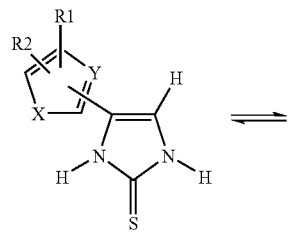

(I)

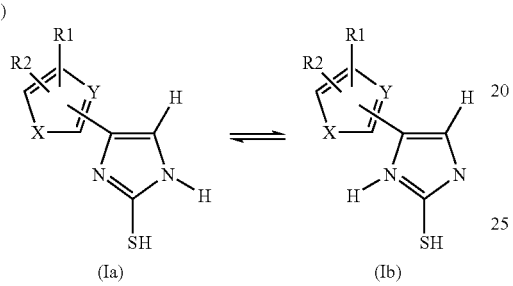

(Ia)   (Ib)

Preferred are, among the addition salts of the compounds of general formula (I) with a pharmaceutically acceptable acid, the salts with an organic acid or with an inorganic acid.

The appropriate inorganic acids are, for example, hydrohalic acids, such as hydrochloric acid or hydrobromic acid, sulfuric acid or nitric acid.

The appropriate organic acids are, for example, picric acid, methanesulfonic acid, ethanesulfonic acid or trifluoromethanesulfonic acid.

The compounds of general formula (I) can also exist in the form of hydrates or of solvates with water or with a solvent.

The appropriate solvents for forming solvates or hydrates are, for example, alcohols, such as ethanol or isopropanol, or water.

According to the present invention, the heterocyclic radical of the compounds according to the invention, of general formula (II):

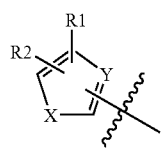

(II)

is selected from among the following heterocycles:

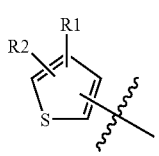

(IIa)

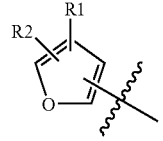

(IIb)

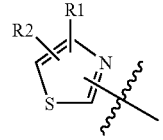

(IIc)

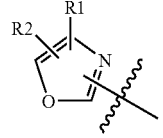

(IId)

According to the present invention, $C_3$-$C_7$ cycloalkyl is a saturated cyclic hydrocarbon chain having from 3 to 7 carbon atoms. Preferably, the $C_3$-$C_7$ cycloalkyl radical is selected from among cyclopropyl, cyclobutyl, cyclopentyl, cyclohexyl and cycloheptyl radicals.

According to the present invention, $C_1$-$C_7$ alkyl is a saturated and linear or branched hydrocarbon chain having from 1 to 7 carbon atoms. Preferably, the $C_1$-$C_7$ alkyl radical is selected from among methyl, ethyl, propyl, isopropyl, butyl, t-butyl, pentyl, hexyl and heptyl radicals.

According to the present invention, $C_1$-$C_4$ alkyl is a saturated and linear or branched hydrocarbon chain having from 1 to 4 carbon atoms. Preferably, the $C_1$-$C_4$ alkyl radical is selected from among methyl, ethyl, propyl, isopropyl, butyl and t-butyl radicals.

According to the present invention, $C_4$-$C_9$ cycloalkylalkyl is a saturated and linear or branched hydrocarbon chain substituted by a cycloalkyl radical and having from 4 to 9 carbon atoms. Preferably, the $C_4$-$C_9$ cycloalkylalkyl radical is selected from among cyclopropylmethyl, cyclopropylethyl, cyclobutylmethyl, cyclobutylethyl, cyclopentylmethyl, cyclopentylethyl, cyclohexylmethyl and cyclohexylethyl radicals.

According to the present invention, ($C_1$-$C_4$ alkoxy)carbonyl is a carboxyl radical substituted by a saturated and linear or branched hydrocarbon chain having from 1 to 4 carbon atoms. Preferably, the ($C_1$-$C_4$ alkoxy)carbonyl radical is selected from among methoxycarbonyl, ethoxycarbonyl, propoxycarbonyl and butoxycarbonyl radicals.

According to the present invention, ($C_1$-$C_6$ alkoxy)carbonyl is a carboxyl radical substituted by a saturated and linear or branched hydrocarbon chain having from 1 to 6 carbon atoms. Preferably, the $C_1$-$C_6$ alkoxy radical is selected from among methoxy, ethoxy, propoxy, butoxy, pentoxy and hexyloxy radicals.

According to the present invention, the compounds of general formula (I) which are particularly preferred are those in which:

R1 is a hydrogen and
R2 is a $C_1$-$C_7$ alkyl radical or a $C_3$-$C_7$ cycloalkyl radical.

According to the present invention, the compounds of general formula (I) which are particularly preferred are those in which the heterocyclic radical of general formula (II) is a thiophene of general formula (IIa).

Among the compounds of general formula (I) according to the present invention, the following compounds are particularly exemplary:

1. 4-(5-ethylthiophen-2-yl)-1,3-dihydroimidazole-2-thione;
2. 4-(5-propylthiophen-2-yl)-1,3-dihydroimidazole-2-thione;
3. 4-(5-methylthiophen-2-yl)-1,3-dihydroimidazole-2-thione;
4. 4-(4-methylthiophen-2-yl)-1,3-dihydro-imidazole-2-thione;
5. 4-(2,5-dimethylthiophen-3-yl)-1,3-dihydroimidazole-2-thione;
6. 4-(3-propylthiophen-2-yl)-1,3-dihydroimidazole-2-thione;
7. 4-(4-propylthiophen-2-yl)-1,3-dihydroimidazole-2-thione;
8. 4-(4-ethylthiophen-2-yl)-1,3-dihydroimidazole-2-thione;
9. 4-(2,5-dimethylfuran-3-yl)-1,3-dihydroimidazole-2-thione;
10. 4-(5-methylfuran-2-yl)-1,3-dihydroimidazole-2-thione;
11. 4-(2,4-dimethylthiazol-5-yl)-1,3-dihydroimidazole-2-thione;
12. 4-(5-cyclopentylthiophen-2-yl)-1,3-dihydroimidazole-2-thione;
13. 4-(5-cyclohexylthiophen-2-yl)-1,3-dihydroimidazole-2-thione;
14. 4-(4-cyclopentylthiophen-2-yl)-1,3-dihydroimidazole-2-thione;
15. 4-(4-cyclohexylthiophen-2-yl)-1,3-dihydroimidazole-2-thione;
16. 4-(5-cyclopropylthiophen-2-yl)-1,3-dihydroimidazole-2-thione;
17. 4-(4-cyclopropylthiophen-2-yl)-1,3-dihydroimidazole-2-thione;
18. 4-(5-cyclopropylmethylthiophen-2-yl)-1,3-dihydroimidazole-2-thione;
19. 4-(5-isobutylthiophen-2-yl)-1,3-dihydroimidazole2-thione;
20. 4-(5-butylthiophen-2-yl)-1,3-dihydroimidazole-2-thione;
21. methyl 5-(2-thioxo-2,3-dihydro-1H-imidazol-4-yl)thiophene-3-carboxylate; and
22. 5-(2-thioxo-2,3-dihydro-1H-imidazol-4-yl)thiophene-3-carboxylic acid.

BRIEF DESCRIPTION OF THE DRAWING

The compounds of general formula (I) are prepared according to the general reaction schemes presented in FIG. 1.

By using the reaction scheme of FIG. 1:

Figure 1:
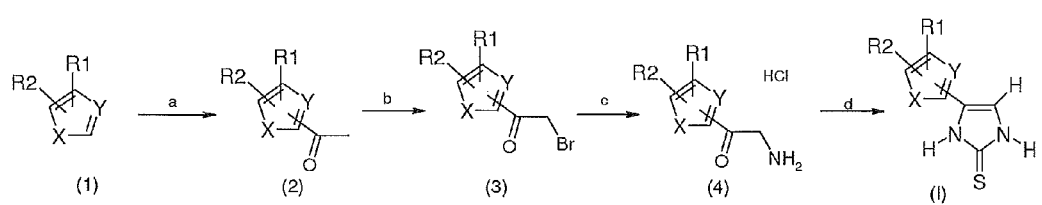

Stage a: the commercially available heterocycles (1) are acetylated according to conventional synthesis conditions, such as, for example, in the presence of acetic anhydride and of phosphoric acid, such as to provide the methyl ketones (2) (Kotha, S.; Kashinath, D.; Lahiri, K.; Sunoj, R. B.; *Eur J Org. Chem.*, 2004, (19), 4003-4013).

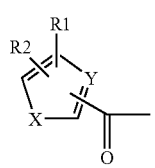

(2)

Stage b: the alpha-bromoketones of general formula (3):

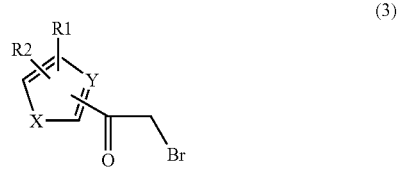

(3)

are commercially available or can be prepared from the methyl ketones (2) according to conventional synthetic methods, such as, for example, through the action of dibromide in a solvent such as dichloromethane (Laufer, S.; Striegel, H.-G.; Neher, K.; Zechmeister, P.; Donat, C.; Stolingwa, K.; Baur, S.; Tries, S.; Kammermeier, T.; Dannhardt, G.; Kiefer, W.; *Arch Pharm.*, 1997, 330 (9), 307-312).

Stage c: the alpha-bromoketones (3) are reacted with sodium diformylamide, for example, in acetonitrile (Yinglin H. and Hongwen H., *Synthesis*, 1990, 615), to give, after hydrolysis of the crude reaction product with hydrochloric acid, for example (Ying-Lin H. and Hong-Wen H. H., *Tetrahedron Lett.*, 1989, 30, 5285), the acylamine hydrochlorides of general formula (4):

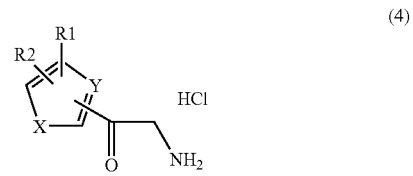

(4)

Stage d: a cyclization reaction of the compounds of general formula (4) using potassium thiocyanate makes it possible to obtain the imidazole-2-thiones of general formula (I) (Mor M., Bordi F., Silva C., Rivara S., Crivori P., Plazzi P. V., Ballabeni V., Caretta A., Barocelli E., Impicciatore M., Carrupt P.-A. and Testa B., *J. Med. Chem.*, 1997, 40 (16), 2571-2578).

Advantageously, the compounds of the present invention exhibit an $IC_{50}$ (dose which inhibits 50% of the enzymatic activity) value with regard to tyrosinase of less than or equal to 10 μM and more particularly of less than or equal to 1 μM.

This invention therefore features formulation of at least one compound of general formula (I) into pharmaceutical or cosmetic compositions exhibiting tyrosinase-inhibiting activity.

This invention also features administration of the compounds of formula (I) for the treatment and/or prevention of pigmentary disorders.

The present invention also features therapeutic or cosmetic treatment regime or regimen comprising the administration, as tyrosinase inhibitor, of a pharmaceutical or cosmetic composition comprising the said compounds of formula (I).

The present invention also features the formulation of a compound of general formula (I) into medicaments useful for the treatment of pigmentary disorders, in particular hyperpigmentary disorders.

This because the compounds according to the invention are particularly appropriate for the treatment and prevention of pigmentary disorders, such as melasma, chloasma, lentigines, senile lentigo, irregular hyperpigmentations related to photoaging, freckles, post inflammatory hyperpigmentations due to an abrasion or to a burn or to a scar or to a dermatosis or to a contact allergy, naevi, genetically determined hyperpigmentations, hyperpigmentations of metabolic or drug origin, melanomas or any other hyperpigmentary lesion.

Another aspect of the present invention is a pharmaceutical composition useful in particular for the treatment of the above-mentioned conditions which comprises, formulated into a pharmaceutically acceptable vehicle compatible with the method of administration selected for the composition, at least one compound of general formula (I) in one of its tautomeric forms or at least one of its salts with a pharmaceutically acceptable acid.

"Pharmaceutically acceptable vehicle" means a medium compatible with the skin, mucous membranes and superficial body growths.

The compositions according to the invention can be administered topically. Preferably, the pharmaceutical composition is packaged in a form suitable for application topically. Topically means administration to the skin or mucous membranes.

The pharmaceutical compositions according to the invention are administered topically, more particularly for the treatment of the skin and mucous membranes and can be provided in the liquid, pasty or solid form and more particularly in the form of ointments, creams, milks, salves, powders, impregnated pads, syndets, solutions, gels, sprays, foams, suspensions, sticks, shampoos or washing bases. Same can also be provided in the form of suspensions of microspheres or nanospheres or of lipid or polymeric vesicles or of polymeric or gelled patches which make possible controlled release.

The compositions for topical application have a concentration of compound according to the invention generally ranging from 0.001% to 10% by weight, preferably from 0.01% to 5% by weight, with respect to the total weight of the composition.

The compounds of general formula (I) according to the invention also find application in the cosmetics field, in particular for protecting against the harmful aspects of the sun, for preventing and/or combating photoinduced or chronological aging of the skin and superficial body growths.

Another aspect of the invention is thus cosmetic compositions comprising, in a cosmetically acceptable vehicle, at least one compound of general formula (I). "Cosmetically acceptable vehicle" means a medium compatible with the skin, mucous membranes and superficial body growths.

Another aspect of the invention is the cosmetic application of a compound of formula (I) or of a composition comprising at least one compound of general formula (I) for preventing and/or treating the signs of skin aging.

Another aspect of the invention is the cosmetic application of a compound of formula (I) or of a composition comprising at least one compound of general formula (I) for body or hair hygiene.

The cosmetic compositions according to the invention comprising, in a cosmetically acceptable vehicle, a compound of general formula (I) or one of its tautomeric forms or one of its salts with a pharmaceutically acceptable acid can be provided in particular in the form of a cream, a milk, a gel, suspensions of microspheres or nanospheres or lipid or polymeric vesicles, impregnated pads, solutions, sprays, foams, sticks, soaps, washing bases or shampoos.

The concentration of compound of general formula (I) in the cosmetic composition preferably ranges from 0.001% to 3% by weight, with respect to the total weight of the composition.

The pharmaceutical and cosmetic compositions as described above can additionally comprise inert additives or even pharmacodynamically active additives, as regards the pharmaceutical compositions, or combinations of these additives, and in particular:

wetting agents;
flavor enhancers;
preservatives, such as para-hydroxybenzoic acid esters;
stabilizers;
moisture regulators;
pH-regulating agents;
osmotic pressure modifiers;
emulsifying agents;
UV-A and UV-B screening agents;
antioxidants, such as α-tocopherol, butylated hydroxyanisole or butylated hydroxytoluene, superoxide dismutase or ubiquinol;
emollients;
moisturizing agents, such as glycerol, PEG 400, thiomorpholinone and its derivatives, or urea;
anti-seborrhoeic or anti-acne agents, such as S-carboxymethylcysteine, S-benzylcysteamine, their salts or their derivatives, or benzoyl peroxide.

Of course, one skilled in the art will take care to select the optional compound or compounds to be added to these compositions such that the advantageous properties intrinsically associated with the present invention are not, or not substantially, detrimentally affected by the envisaged addition.

To further illustrate the present invention and the advantages thereof, the following specific examples are given, including those indicating biological activity, it being understood that same are intended only as illustrative and in nowise limitative. In said examples to follow, all parts and percentages are given by weight, unless otherwise indicated.

Example 1

4-(5-Ethylthiophen-2-yl)-1,3-dihydroimidazole-2-thione 1-(5-ethylthiophen-2-yl)ethanone In a 50 ml three-necked flask, 5 g (44.6 mmol, 1 eq) of 2-ethylthiophene are dissolved in 28 ml of acetic anhydride, 0.5 ml of ortho-phosphoric acid are added and the reaction mixture is then heated for 1 hour at 80° C. The acids are evaporated off under reduced pressure, and the oil obtained is then filtered over a silica patch (eluent: 20% ethyl acetate, 80% heptane) after evaporation of the solvents: 5.2 g of 1-(5-ethylthiophen-2-yl)ethanone are obtained in the form of a brown oil. Yield: 76%.

2-Bromo-1-(5-ethylthiophen-2-yl)ethanone

In a 100 ml three-necked flask at ambient temperature and under nitrogen, 5.2 g (33.7 mmol, 1 eq) of 1-(5-ethylthiophen-2-yl)ethanone are dissolved in 50 ml of dichloromethane, and 2 ml (38.8 mmol, 1.15 eq) of dibromine are added dropwise. The reaction mixture is stirred for 16 hours at ambient temperature and then for 3 hours at 45° C. The reaction medium is transferred into 100 ml of a sodium thiosulfate solution and then extracted with 100 ml of dichloromethane, the organic phase is dried over magnesium sulfate, and the solvents are then evaporated off. The residue is filtered over a silica patch; eluent: 20% ethyl acetate and 80% heptane. 8 g of a brown oil are obtained. The preceding oil is solubilized in 24 ml of tetrahydrofuran and cooled to 0° C. 0.84 ml of diethyl phosphite and 0.92 ml of triethylamine are added to the reaction mixture. The mixture is stirred for 1 hour at 0° C. and then for 4 hours at ambient temperature. The reaction medium is poured into 200 ml of ice-cold water and then extracted with 200 ml of ethyl acetate. The organic phases are dried over magnesium sulfate and the residue is then chromatographed on silica gel (5% ethyl acetate/95% heptane). 5 g of 2-bromo-1-(5-ethylthiophen-2-yl)ethanone are obtained in the form of orangey-yellow oil. Yield=63%

2-(5-Ethylthiophen-2-yl)-2-oxoethylammonium

In a 100 ml three-necked flask at ambient temperature and under nitrogen, 2.7 g (11.6 mmol) of 2-bromo-1-(5-ethylthiophen-2-yl)ethanone are dissolved in 50 ml of acetonitrile, 1.21 g (12.75 mmol) of sodium diformamide are added and the mixture is then stirred for 48 hours at ambient temperature. The reaction medium is filtered and the residue is then taken up in 40 ml of a 1M solution of hydrochloric acid in ethanol and heated at 50° C. for 4 hours. The solvents are evaporated off and then 30 ml of diethyl ether are added. The solid is filtered off to give 2.2 g of 2-(5-ethylthiophen-2-yl)-2-oxoethylammonium in the form of a beige solid. Yield: 91%.

4-(5-Ethylthiophen-2-yl)-1,3-dihydroimidazole-2-thione

In a 50 ml three-necked flask at ambient temperature and under nitrogen, 4.51 g (93 mmol) of potassium thiocyanate are dissolved in 22 ml of water in the presence of 3.2 ml of 1M hydrochloric acid, and then 2.17 g (10.3 mmol) of 2-(5-ethylthiophen-2-yl)-2-oxoethylammonium are added. The reaction medium is stirred at reflux until the starting product has disappeared. The precipitate is filtered off and then washed with water and ethyl acetate: 0.9 g of a yellowy-ochre solid is obtained. After recrystallization from ethyl acetate, 0.42 g of 4-(5-ethylthiophen-2-yl)-1,3-dihydroimidazole-2-thione is obtained in the form of a light yellow solid. Yield: 20%.

$^1$H NMR (DMSO, 400 MHz): 1.21 (t, 3H, J=7 Hz, $CH_3$); 2.75 (q, 2H, J=7 Hz, $CH_2$); 6.75 (m, 1H, CH); 7.05 (s, 1H, CH); 7.17 (m, 1H, CH); 12.0 (s, 1H, NH); 12.5 (s, 1H, NH).
$^{13}$C NMR (DMSO, 100 MHz): 16.2, 23.1, 111.4, 124.0, 124.6, 124.7, 128.1, 146.1, 161.9.

In a manner analogous to the preceding example, the following are obtained:

Example 2

4-(5-Propylthiophen-2-yl)-1,3-dihydroimidazole-2-thione $^1$H NMR (DMSO, 400 MHz): 1.04 (t, 3H, J=7 Hz, $CH_3$); 1.73 (m, 2H, $CH_2$); 2.84 (t, 2H, J=7 Hz, $CH_2$); 6.87 (m, 1H, CH); 7.19 (s, 1H, CH); 7.30 (m, 1H, CH); 12.1 (s, 1H, NH); 12.7 (s, 1H, NH).
$^{13}$C NMR (DMSO, 100 MHz): 13.9, 24.8, 31.7, 111.4, 124.0, 124.6, 125.5, 128.3, 144.2, 161.9.

Example 3

4-(5-Methylthiophen-2-yl)-1,3-dihydroimidazole-2-thione $^1$H NMR (DMSO, 400 MHz): 2.41 (s, 3H, $CH_3$); 6.72 (s, 1H, CH); 6.91 (s, 1H, CH); 7.15 (s, 1H, CH); 12.0 (s, 1H, NH); 12.5 (s, 1H, NH).
$^{13}$C NMR (DMSO, 100 MHz): 15.3, 111.4, 124.2, 124.4, 126.4, 128.5, 138.6, 161.8.

Example 4

4-(4-Methylthiophen-2-yl)-1,3-dihydro-imidazole-2-thione $^1$H NMR (DMSO, 400 MHz): 2.17 (s, 3H, $CH_3$); 7.02 (s, 1H, CH); 7.12 (s, 1H, CH); 7.19 (s, 1H, CH); 12.1 (s, 1H, NH); 12.6 (s, 1H, NH).
$^{13}$C NMR (DMSO, 100 MHz): 15.8, 111.9, 120.2, 124.4, 126.4, 130.5, 138.0, 162.0.

Example 5

4-(2,5-Dimethylthiophen-3-yl)-1,3-dihydro-imidazole-2-thione $^1$H NMR (DMSO, 400 MHz): 2.37 (2s, 6H, $CH_3$); 6.93 (s, 1H, CH); 6.98 (s, 1H, CH); 12.1 (s, 1H, NH); 12.3 (s, 1H, NH).
$^{13}$C NMR (DMSO, 100 MHz): 14.2, 14.7, 112.3, 124.8, 125.0, 125.3, 131.6, 135.0, 160.5.

Example 6

4-(3-Propylthiophen-2-yl)-1,3-dihydro-imidazole-2-thione $^1$H NMR (DMSO, 400 MHz): 0.86 (t, 3H, J=7 Hz, $CH_3$); 1.55 (hex, 2H, J=7 Hz, $CH_2$); 2.56 (t, 2H, J=7 Hz, $CH_2$); 6.96 (s, 1H, CH); 7.02 (d, 1H, J=5 Hz, CH); 7.51 (d, 1H, J=5 Hz, CH); 12.2 (sI, 2H, NH).
$^{13}$C NMR (DMSO, 100 MHz): 13.9, 22.9, 30.4, 113.9, 122.0, 123.6, 125.3, 129.3, 140.7, 161.1.

Example 7

Tyrosinase Activity Inhibition Assay

The activity of the inhibitors is measured starting from a lysate of B16F1 cells (murine melanoma line). In the presence of the L-tyrosine substrate, the tyrosinase present in these cells catalyses the hydroxylation of L-tyrosine to give L-DOPA and then the oxidation of the L-DOPA to give dopaquinone. In the presence of MBTH (3-methyl-2-benzothiazolinone hydrazone), the dopaquinone is trapped so as to form a pink complex which absorbs at 520 nm.

The B16F1 cells are cultured in DMEM medium+10% foetal calf serum+$10^{-9}$ M α-MSH for 4 days at 37° C. under 7% $CO_2$. They are treated with trypsin, washed with PBS, counted and pelleted. The pellet is taken up at $10^7$ cells/ml in lysis buffer (10 mM sodium phosphate, pH 6.8-1% Igepal) and the suspension is treated with ultrasound for 10 seconds. After centrifugation for 30 minutes at 4000 rpm, the supernatant obtained constitutes the cell lysate used as tyrosinase source in the enzymatic assay.

The assays are carried out in duplicate in 384-well plates in a total volume of 50 μl. Each well contains:
  40 μl of solution containing 1.25 mM L-tyrosine, 6.25 μM L-DOPA (cofactor) and 3.75 mM MBTH in buffer B (62.25 mM sodium phosphate, pH 6.8-2.5% dimethylformamide),
  5 μl of inhibitor diluted in DMSO,
  5 μl of cell lysate diluted to ½ in 50 mM Tris HCl buffer, pH 7.5.

The plate is incubated at 37° C. and a spectrophotometric reading is carried out at 520 nm after incubating for 6 hours.

To avoid any possible absorption of the products, the system uses corrected absorbance (absorbance at time 6 h—absorbance at time zero).

The inhibitors are assayed in terms of dose-response so as to calculate an $IC_{50}$ (dose which inhibits 50% of the enzymatic activity).

Several internal controls are added to each experiment:
control for 100% activity: the 5 µl of inhibitor are replaced with 5 µl of DMSO,
control for 50% activity: the 5 µl of inhibitor are replaced with 5 µl of phenylthiourea at 300 µM in DMSO,
control for 0% activity: the L-tyrosine substrate is replaced with buffer B.

The results obtained for the compounds of the invention are presented in Table A:

TABLE A

| Name | Structure | Tyrosine hydroxylase/Dopa oxidase $IC_{50}$ (µM) |
|---|---|---|
| Compound 3 | 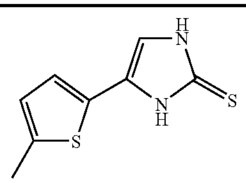 | 0.3 |
| Compound 4 | 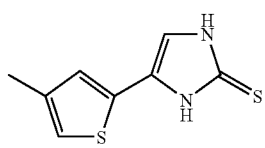 | 0.1 |

Example 8

Formulations

In this example, various specific formulations based on the compounds according to the invention have been illustrated.

Topically:

(a) Ointment:

| | |
|---|---|
| Compound 1 | 0.020 g |
| Isopropyl myristate | 81.700 g |
| Liquid petrolatum | 9.100 g |
| Silica ("Aerosil 200") | 9.180 g |

(b) Ointment:

| | |
|---|---|
| Compound 6 | 0.300 g |
| White petrolatum, pharmaceutical grade | q.s. for 100 g |

(c) Nonionic Water-in-Oil Cream:

| | |
|---|---|
| Compound 1 | 0.100 g |
| Mixture of emulsive lanolin alcohols, of waxes and of oils ("Anhydrous eucerin") | 39.900 g |
| Methyl para-hydroxybenzoate | 0.075 g |
| Propyl para-hydroxybenzoate | 0.075 g |
| Sterile demineralized water | q.s. for 100 g |

(d) Lotion:

| | |
|---|---|
| Compound 6 | 0.100 g |
| Polyethylene glycol (PEG 400) | 69.900 g |
| 95% Ethanol | 30.000 g |

(e) Hydrophobic Ointment:

| | |
|---|---|
| Compound 2 | 0.300 g |
| Isopropyl myristate | 36.400 g |
| Silicone oil ("Rhodorsil 47 V 300") | 36.400 g |
| Beeswax | 13.600 g |
| Silicone oil ("Abil 300 000 cst") | q.s. for 100 g |

(f) Nonionic Oil-in-Water Cream:

| | |
|---|---|
| Compound 4 | 1.000 g |
| Cetyl alcohol | 4.000 g |
| Glycerol monostearate | 2.500 g |
| PEG 50 stearate | 2.500 g |
| Shea butter | 9.200 g |
| Propylene glycol | 2.000 g |
| Methyl para-hydroxybenzoate | 0.075 g |
| Propyl para-hydroxybenzoate | 0.075 g |
| Sterile demineralized water | q.s. for 100 g |

Each patent, patent application, publication, text and literature article/report cited or indicated herein is hereby expressly incorporated by reference in its entirety.

While the invention has been described in terms of various specific and preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A 4-heteroarylimidazole-2-thione tyrosinase inhibiting compound of general formula (I):

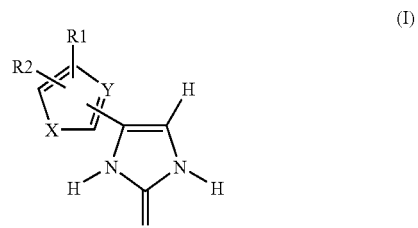

(I)

in which:
X is an oxygen atom or a sulfur atom,
Y is a carbon atom or a nitrogen atom,
when R2=H, then R1 is:
a $C_1$-$C_7$ alkyl radical,
a $C_3$-$C_7$ cycloalkyl radical, with the proviso that one of the carbon atoms of the ring may optionally be replaced by an oxygen or sulfur atom,
a $C_4$-$C_9$ cycloalkylalkyl radical,
a carboxyl substituent,
a ($C_1$-$C_6$ alkoxy)carbonyl radical, or a C$_1$-C$_4$ alkyl radical substituted by a (C$_1$-C$_4$ alkoxy) carbonyl, and, when R2 is other than a hydrogen atom, then R$_1$ and R$_2$, which may be identical or different, are selected from among:
- a C$_1$-C$_7$ alkyl radical,
- a C$_3$-C$_7$ cycloalkyl radical, with the proviso that one of the carbon atoms of the ring may optionally be replaced by an oxygen or sulfur atom,
- a C$_4$-C$_9$ cycloalkylalkyl radical,
- a carboxyl substituent,
- a (C$_1$-C$_6$ alkoxy)carbonyl radical, or
- a C$_1$-C$_4$ alkyl radical substituted by a (C$_1$-C$_4$ alkoxy) carbonyl radical, and, when R2 is in the ortho position with respect to R1, then R1 and R2 together form a hydrocarbon ring containing 5 or 6 carbon atoms,
and the salts and tautomeric forms thereof.

2. A compound as defined by claim 1, in the form of a salt formed with an acid selected from among inorganic acids and organic acids.

3. A compound as defined by claim 1, wherein a heterocyclic radical of general formula (II):

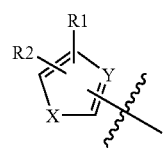

(II)

comprises a thiophene of general formula (IIa):

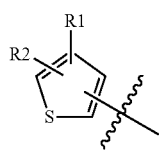

(IIa)

4. A compound as defined by claim 1, wherein R1 is a hydrogen atom and R2 is a C$_1$-C$_7$ alkyl radical or a C$_3$-C$_7$ cycloalkyl radical.

5. A compound as defined by claim 1, selected from the group consisting of:
1. 4-(5-ethylthiophen-2-yl)-1,3-dihydroimidazole-2-thione;
2. 4-(5-propylthiophen-2-yl)-1,3-dihydroimidazole-2-thione;
3. 4-(5-methylthiophen-2-yl)-1,3-dihydroimidazole-2-thione;
4. 4-(4-methylthiophen-2-yl)-1,3-dihydroimidazole-2-thione;
5. 4-(2,5-dimethylthiophen-3-yl)-1,3-dihydroimidazole-2-thione;
6. 4-(3-propylthiophen-2-yl)-1,3-dihydroimidazole-2-thione;
7. 4-(4-propylthiophen-2-yl)-1,3-dihydroimidazole-2-thione;
8. 4-(4-ethylthiophen-2-yl)-1,3-dihydroimidazole-2-thione;
9. 4-(2,5-dimethylfuran-3-yl)-1,3-dihydroimidazole-2-thione;
10. 4-(5-methylfuran-2-yl)-1,3-dihydroimidazole-2-thione;
11. 4-(2,4-dimethylthiazol-5-yl)-1,3-dihydroimidazole-2-thione;
12. 4-(5-cyclopentylthiophen-2-yl)-1,3-dihydroimidazole-2-thione;
13. 4-(5-cyclohexylthiophen-2-yl)-1,3-dihydroimidazole-2-thione;
14. 4-(4-cyclopentylthiophen-2-yl)-1,3-dihydroimidazole-2-thione;
15. 4-(4-cyclohexylthiophen-2-yl)-1,3-dihydroimidazole-2-thione;
16. 4-(5-cyclopropyl-thiophen-2-yl)-1,3-dihydroimidazole-2-thione;
17. 4-(4-cyclopropylthiophen-2-yl)-1,3-dihydroimidazole-2-thione;
18. 4-(5-cyclopropylmethylthiophen-2-yl)-1,3-dihydroimidazole-2-thione;
19. 4-(5-isobutylthiophen-2-yl)-1,3-dihydroimidazole2-thione;
20. 4-(5-butylthiophen-2-yl)-1,3-dihydroimidazole-2-thione;
21. methyl 5-(2-thioxo-2,3-dihydro-1H-imidazol-4-yl)thiophene-3-carboxylate; and
22. 5-(2-thioxo-2,3-dihydro-1H-imidazol-4-yl)thiophene-3-carboxylic acid.

6. A regime or regimen for the treatment or prevention of hyperpigmentary disorders, comprising topically applying onto the skin, mucous membranes and/or superficial body growths of an individual in need of such treatment, a thus effective amount of at least one compound as defined in claim 1, or salt or tautomeric form thereof, formulated into a topically applicable, pharmaceutically acceptable vehicle therefor.

7. The regime or regimen defined by claim 6, wherein said hyperpigmentary disorders are selected from among melasma, chloasma, lentigines, senile lentigo, irregular hyperpigmentations related to photoaging, freckles, post inflammatory hyperpigmentations due to an abrasion or to a burn or to a scar or to a dermatosis or to a contact allergy, naevi, genetically determined hyperpigmentations, hyperpigmentations of metabolic or drug origin and melanomas.

8. A topically applicable pharmaceutical composition useful for the treatment and/or prevention of hyperpigmentary disorders, comprising at least one compound of general formula (I) as defined by claim 1, formulated into a topically applicable, pharmaceutically acceptable vehicle therefor.

9. The composition as defined by claim 8, wherein the concentration of compound of general formula (I) ranges from 0.001% to 10% by weight, with respect to the total weight of the composition.

10. The composition as defined by claim 9, wherein the concentration of compound of general formula (I) ranges from 0.01% to 5% by weight, with respect to the total weight of the composition.

11. A cosmetic composition comprising, formulated into a cosmetically acceptable vehicle, at least one compound of general formula (I) as defined by claim 1.

12. The composition as defined by claim 11, wherein the concentration of compound of general formula (I) ranges from 0.001% to 3% by weight, with respect to the total weight of the composition.

13. The regime or regimen as defined by claim 6, for preventing and/or treating signs of skin aging.

14. The regime or regimen as defined by claim 6, for body or hair hygiene.

* * * * *